United States Patent [19]
Tirelli et al.

[11] Patent Number: 5,050,200
[45] Date of Patent: Sep. 17, 1991

[54] RADIATION CONTROL DEVICE WITH VARIABLE ACTIVE SURFACE

[75] Inventors: Marco Tirelli, Villebon sur Yvette; René Romeas, Palaiseau; Yves Gregoire, Paris, all of France

[73] Assignee: General Electric CGR S.A., Issy les Moulineaux, France

[21] Appl. No.: 514,963

[22] Filed: Apr. 26, 1990

[30] Foreign Application Priority Data
Apr. 28, 1989 [FR] France .................................. 89 05663

[51] Int. Cl.$^5$ ............................ G21K 1/04; A61B 6/04
[52] U.S. Cl. ...................................... 378/149; 378/145; 378/147; 378/148; 378/16; 378/10; 378/37
[58] Field of Search .................... 378/37, 98, 94, 4, 10, 378/8, 16, 63, 64, 96, 97, 98, 112, 117, 147, 148, 149, 150, 156, 159, 186, 205, 210, 108, 7, 160, 187

[56] References Cited
U.S. PATENT DOCUMENTS
4,577,341  3/1986  Schwieker et al. ................. 378/150
4,691,335  9/1987  Telorack ............................ 378/150

Primary Examiner—Edward P. Westin
Assistant Examiner—Don Wong
Attorney, Agent, or Firm—Oblon, Spivak, McClelland, Maier & Neustadt

[57] ABSTRACT

Disclosed is a radiology system of the mammography type wherein there is provision for a radiation controller having a detector of X-radiation having gone through the breast to be observed, of the type having a converter of X-radiation into photon radiation and a photomultiplier tube for the amplifications of photons emitted by the converter. The invention lies in the fact that the converter is masked by a belt opaque to the photon radiation except in the zones for which variable dimensions are planned so as to get adapted to the different shapes of breasts. The belt is driven by a motor which is turned on and off at the practitioner's command, so that the appropriate zone is in correspondence with the converter.

2 Claims, 2 Drawing Sheets

RADIATION CONTROL DEVICE WITH VARIABLE ACTIVE SURFACE

BACKGROUND OF THE INVENTION

1. Field of the Invention

The invention concerns radiology systems, such as mammographs and, more particularly in such systems, a device that can be used to control the dose of radiation received by a person during examination as well as the exposure time so as to obtain an image with the optimum contrast.

2. Description of the Prior Art

As shown in FIG. 1, radiology systems of the mammography type comprise an X-radiation source 10, borne by a bracket 11 placed at the top of a vertical plate 12. This plate has an assembly 13 on which the breast 16 to be examined rests by means of a horizontal shelf 15. A pad 17, transparent to X-radiation and vertically movable on the plate 12, is used to compress the breast.

To get adapted to the patient's size, the plate 12 is mounted on a vertical column 9 resting on the ground, and moves vertically on said column by means of an appropriate mechanical device.

On its upper part and beneath the shelf 15, the assembly 13 has a tunnel in which there is housed a cartridge 18 formed by a black box enclosing a film 14 sensitive to the direct X-radiation or to a photon radiation emitted by a screen (not shown) receiving the X-radiation. It is on this film 14 that the latent image of the breast is formed after an appropriate exposure time. The development of the film gives an X-ray photograph.

For the photograph to be useful for the purposes of diagnosis, all the points that form the image of the examined object should have sufficient contrast with one another. In particular, the blackening of the film should be right and "standardized" for a very wide range of opacity of the object. To this effect, the blackening may be controlled by a radiation control device which is placed beneath the cartridge in the lower part 8 of the assembly 13. This control device, also called an exposer, is formed essentially by an X-radiation detector that delivers an electrical signal proportionate to the flow-rate of the dose of X-radiation that passes through the sensitive film. This electrical signal, which expresses the intensity of the X-radiation, is integrated during the exposure time, and the signal resulting from this integration is compared at each instant with a pre-determined threshold signal which is a function of the characteristics of the sensitive film. As soon as the integrated signal reaches this threshold, the signal indicating equality controls the source to be turned-off, and this ends the exposure time.

One of the advantages of this radiation control device is that, for a wide-ranging variation in the X-radiation flow-rates leading to differences in exposure, it makes it possible, firstly, to obtain an exposure of sensitive film corresponding to an optimum contrast and, secondly, to have more efficient control over the mean dose received by the patient, this dose being a major factor in the assessment of carcinogenic risk.

In a radiation control device, it is important that the detector should receive only the radiation that has gone through the breast, for the reception of an unattenuated radiation would falsify the measurement. Hence, the receiving surface of a detector such as this is limited by the size of the smallest breast to be examined. A limitation of this kind would considerably restrict the advantages that might be drawn from this device, and would constitute a factor of error in certain circumstances, for the zone of the object corresponding to the size of the detector may be different from the one examined. For, the position of the detector is generally fixed whereas the zone to be examined may have a position that is variable with respect to that of the detector and, therefore, there is not the overlapping desired for an optimum measurement.

This limitation is even more pronounced in mammography for there is great disparity among the individuals observed and, for one and the same individual, there is a disparity depending on the instant at which the examination is performed in relation to the hormone cycle. In the first category, there are anatomical differences such as the size of the breast and the local composition of the tissues. In the second category, there is the composition and distribution of the tissues as a function of the hormone cycle, age, weight and somatic development. In addition, there is the density and distribution of the structures to be displayed, whether they are pathological or not, whether they are massive or whether they are micro-calcifications, the positions of which are not known to the practitioner.

In short, with a small-sized detector having a fixed position, the measuring signal does not represent the breast in its entirety and may lead to under-exposed photographs when the detector is beneath an adipose part of the breast or over-exposed photographs when the detector is beneath a fibrous part or beneath a region of pathological opacity.

Owing to the above-mentioned inadequacies, it will be difficult for the practitioner to use the photographs obtained to make a diagnosis or a preventive check-up with a high degree of certainty. He will therefore be led to repeat the examination so that the advantages of the use of a detector, namely speed, greater contrast, reduction in the dose of radiation and reduction in kinematic blur, are jeopardized.

These drawbacks are partially attenuated in systems where the entire detector assembly can be shifted in its plane beneath the breast. However, there is a limit to the greatest possible dimension of the detector and, consequently, this detector is badly optimized with respect to the different sizes of breast encountered. In this case, the signal resulting from the integration is an approximation of the optimum signal: it is therefore experience that must guide the practitioner in his choice of the position of the detector.

Besides, it is hardly possible to predict the position at which the regions of opacity will be located on the photograph, whence the difficulty of choosing the position of the cell in the first photograph.

SUMMARY OF THE INVENTION

The aim of the present invention, therefore, is the making of a radiation control device that can be adapted to different sizes of the object to be X-rayed, especially when it is a breast.

To this effect, the invention proposes, firstly, the enlargement of the dimensions of the detector up to, possibly, the dimensions of the sensitive film and, secondly, the use of masks of different dimensions that are placed between the cartridge and the detector.

The invention relates to a device for the control of radiation in a radiology system that comprises at least one source of X-radiation and one detector of the X-radiation that has gone through an object to be observed, of the type having a converter of X-radiation into photon radiation and a photomultiplier tube for the photons emitted by the converter, said detector giving an electric signal used to control the time of exposure of the object, said device further comprising at least one mask, opaque to light radiation but transparent to X-radiation, interposed between the radiation converter and the photomultiplier, said mask having at least one zone transparent to light radiation, the shape and the area of the transparent zone being adapted to the dimensions of the object to be observed or to the type of examination that is performed.

The mask is supported by a belt which is associated with a mechanism for the shifting of said belt so as to place said transparent zone in an optimal position with respect to the object.

Furthermore, this belt has several zones transparent to the light radiation which are arranged successively in the direction in which the belt is shifted, the dimensions and shape of these zones being different from one zone to the next one so as to get adapted to the dimensions and shape of the object as well as to the type of examination performed.

BRIEF DESCRIPTION OF THE DRAWINGS

Other characteristics and advantages of the present invention will appear from the following description of a particular embodiment, said description being made with reference to the appended drawings, wherein.

DESCRIPTION OF A PREFERRED EMBODIMENT

Figure 1:
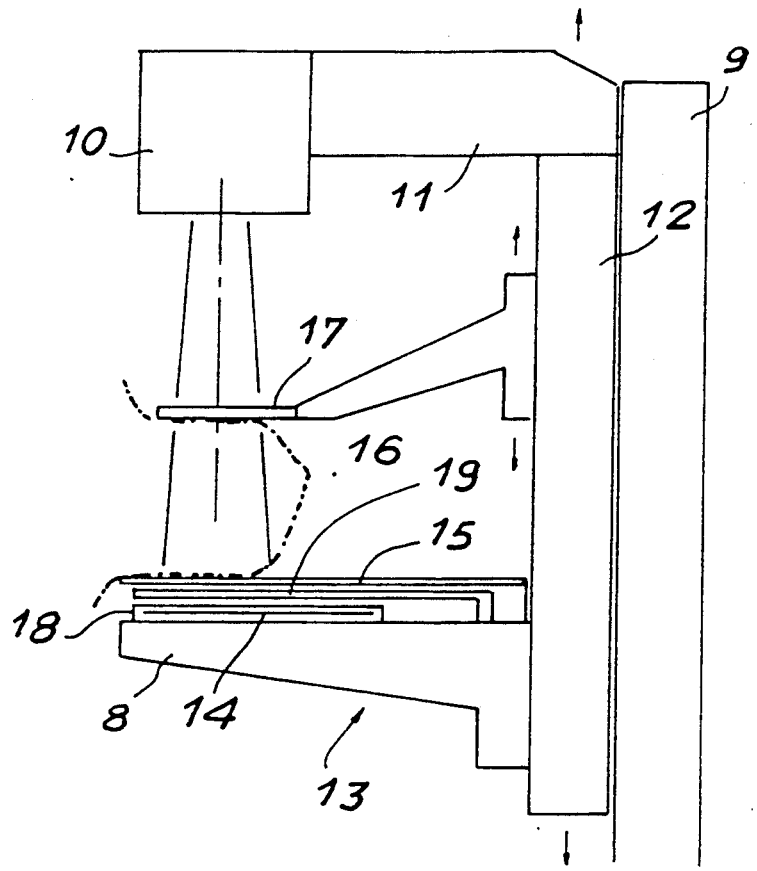
FIG. 1 shows a vertical section of a mammograph in a plane passing through the source of the X-radiation.
Figure 2:
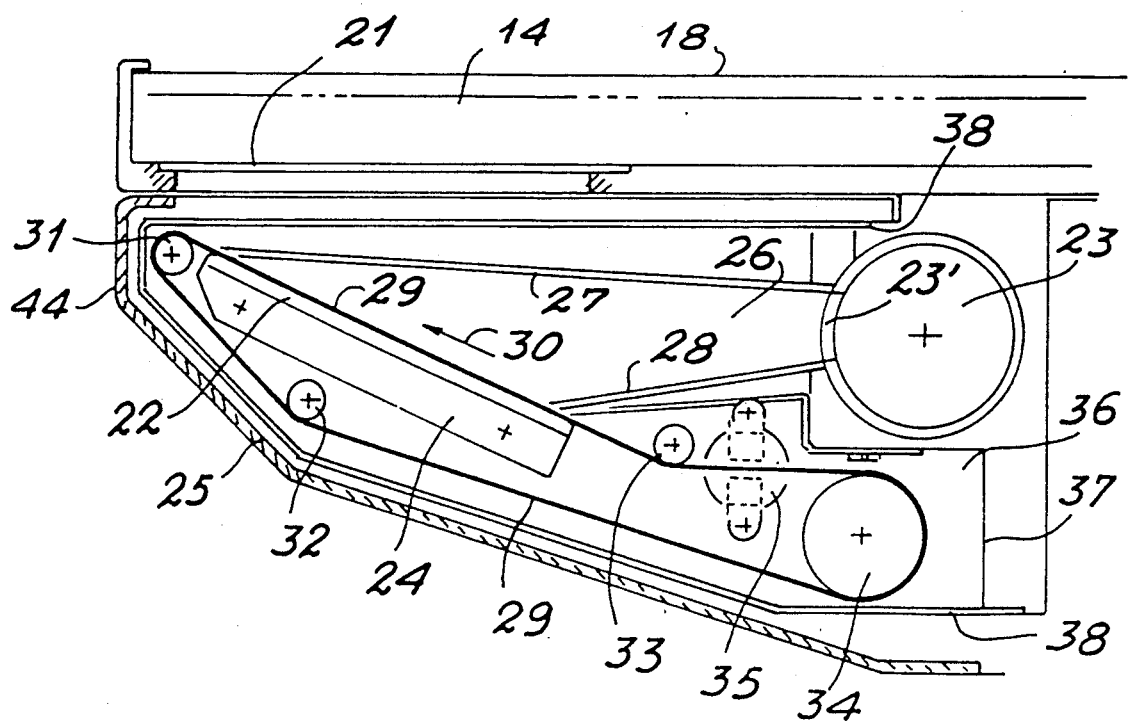
FIG. 2 shows a vertical section of an embodiment of an automatic mask-changing device.

The invention shall be described in its application to a mammograph, but it can be implemented in other systems of radiology where use is made of a radiation controller of the type having a converter of X-radiation into photon radiation and a photomultiplier tube for the photons emitted by the converter. In order to adapt the radiation control more efficiently to the zone to be examined, irrespectively of the size of the breast, the invention proposes the control of the surface of the active zone of the radiation converter through the interposition, between this converter and the photomultiplier tube, of a mask opaque to the light radiation, having transparent windows with dimensions and shapes that vary as a function of those of the breast to be examined.

To achieve this kind of an interposition of masks, the invention proposes an automatic device for the shifting of the masks.

The automatic device is positioned in the lower part 8 of the assembly 13 beneath the cartridge 18. This cartridge 18 has, in a known way, a sensitive film 14 inside the black box formed by the cartridge and a zone 21 transparent to X-radiation, located in the lower wall of the cartridge and in the vicinity of the external edge of the part 8 closest to the patient. The radiation converter is formed by a screen 22 which emits photons towards a photomultiplier 23 when it receives X-radiation going through the transparent zone 21.

The screen 22 is fixed to a support 24, fixedly joined to a frame 25, formed essentially by the lower part 8 of the assembly 13. The photons emitted by the screen 22 are focused on the input 23' of the photomultiplier 23 by a conduct 26 comprising notably the walls 27 and 28, opaque to light but transparent to X-radiation.

Before the screen 22, there is placed a belt 29 which is supported and driven in motion in the direction of the arrow 30 by a driving motor 34 and supporting rollers 31, 32 and 33. A mechanism 35 enables the belt 29 to be positioned and its tension to be adjusted. The belt gets shifted in a black box 36 that has the walls 28, 37 and 38 so that the external light does not disturb the measurement of the photomultiplier 23.

Figure 3:
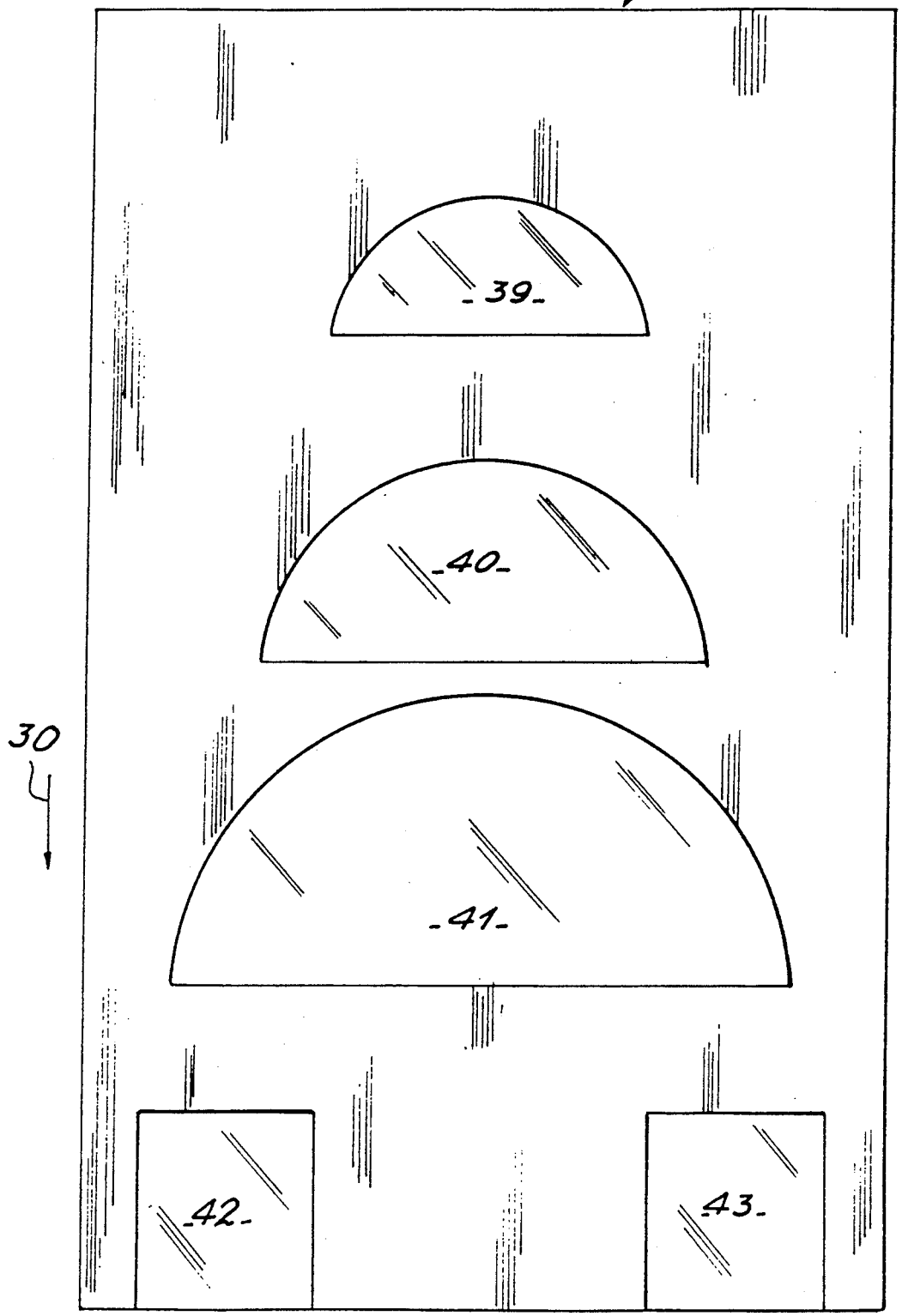
FIG. 3 is an spread-out view of the belt bearing the different masks.

The belt 29 is a loop and is opaque to the light radiation throughout its surface, except for the zones 39, 40, 41, 42 and 43 (FIG. 3). The zones 39, 40 and 41 have a general shape of a semi-circle, the diameter of which varies from one zone to the next, the zone 39 with the smallest diameter being intended, for example, for the examination of small breasts, the zone 40 for the examination of medium-sized breasts and the zone 41 for the examination of big breasts. Finally, the zones 42 and 43, which are rectangular and are positioned symmetrically on either side of the longitudinal axis of symmetry 44 of the belt, are used during a stereotaxic examination to obtain two views on the same film.

Depending on the length of the belt 29, it is possible to create a number of windows, such as 39, 40 and 41, that is greater than three in order to cover differences in breast sizes more efficiently. Furthermore, these zones may have shapes other than that of a semi-circle. Clearly, the maximum dimensions of the window 41 or of the rectangle encompassing the windows 42 and 43 are those of the screen associated with the photomultiplier 23.

In the course of an examination, the choice of the window adapted to the breast being observed is made by the practitioner, and the electric control circuit for the driving motor 34 is designed to position the chosen window before the screen 22, the base of the semi-circle being located towards the external edge 44 of the part 8 of the assembly 13, as close as possible to the patient. The invention that has just been described thus enables the practitioner to adapt the exposure time and hence the dose of radiation emitted as a function, notably, of the size of the breast to be examined.

What is claimed is:

1. A device for the control of radiation in a radiology system that comprises at least one source of X-radiation and one detector of the X-radiation that has gone through an object to be observed, of the type having a converter of X-radiation into photon radiation and a photomultiplier tube for the amplification of photons emitted by the converter, said detector giving an electric signal used to control the time of exposure of the object, said device further comprising:

at least one mask supported by a movable belt, which is opaque to light radiation, but transparent to X-radiation, and which is interposed between the radiation converter and the photomultiplier, said mask having at least one zone transparent to light radiation, the shape and the area of the transparent zone being adapted to the dimensions of the object to be observed or to the type of examination that is performed wherein;

said supporting movable belt has several transparent zones with respect to light transmission and which are arranged in successive position of said belt with each of these zones being different from one zone to the next.

2. A device for the control of radiation in a radiology system comprising:
- at least one source of X-radiation and one detector of the X-radiation that has gone through an object to be observed;
- a X-radiation converter means for converting X-radiation into photon radiation;
- a photomultiplier tube for the amplification of photons emitted by said means for converting;
- means for coupling said detector such that an electric signal is produced which is used to control the time of exposure of the object;
- at least one mask, opaque to light radiation but transparent to X-radiation, interposed between the X-radiation converter means and the photomultiplier tube, said mask having at least one zone transparent to light radiation, the shape and the area-of the transparent zone being adapted to the dimensions of the object to be observed or to the type of examination that is performed;
- a means to support said mask by a belt; and
- a mechanism for the shifting of said belt so as to place transparent zone in an optimal position with respect to the object;
- wherein the belt has several zones transparent to the light radiation which are arranged successively in the direction in which the belt is shifted, the dimensions and shape of these zones being different from one zone to the next one so as to get adapted to the dimensions and to the shape of the object.

* * * * *